US005799660A

United States Patent [19]
Bertone

[11] Patent Number: 5,799,660
[45] Date of Patent: Sep. 1, 1998

[54] METHODS FOR EVALUATING EFFICACY OF ANTI-INFLAMMATORY ON DRUGS ON JOINT INFLAMMATION

[75] Inventor: Alicia L. Bertone, Columbus, Ohio

[73] Assignee: The Ohio State Research Foundation

[21] Appl. No.: 599,251

[22] Filed: Feb. 9, 1996

[51] Int. Cl.$^6$ .................................................. A61B 00/19
[52] U.S. Cl. .......................... 128/898; 604/27; 604/28; 435/1.2
[58] Field of Search ........................... 128/898; 435/1.1, 435/1.2; 604/27–45

[56] References Cited

U.S. PATENT DOCUMENTS 3,914,954 10/1975 Doerig .............................. 435/284.1
4,192,302 3/1980 Boddie ........................................ 604/4

OTHER PUBLICATIONS

"Physiologic Responses of a Novel Isolated Joint Model" by Bertone, et al., (short poster page) *Transactions of the 41st Annual Meeting of Orthopaedic Research Society*, Feb. 1995, p. 796.

"Blood Flow, Permeability, and $O_2$ Metabolism of Innervated or Denervated Isolated Joints in an IL–1 Model" (short poster page) *Transactions of the 42nd Annual Meeting of Orthopaedic Research Society* Feb. 1996 p. 429.

"Evaluation of Vascular Compliance and Vasoconstrictive Reactions in Amputated Hindlimbs of Rats" by Ono, et al., *Journal of Orthopaedic Research*, vol. 13, pp. 375–381, May 1995.

"Evaluation of Starling Forces in the Equine Digit", Allen, et al., *Journal of Applied Physiology*, vol. 64, No. 4, pp. 1580–1583, Apr. 1988.

*Primary Examiner*—Vincent Millin
*Assistant Examiner*—Kelly O'Hara
*Attorney, Agent, or Firm*—Calfee, Halter & Griswold LLP

[57] ABSTRACT

The present invention provides methods for: detecting and quantifying the release of chemical agents, such as anti-inflammatory drugs from the synovial cavity of a joint into the vascular system of the joint; directly measuring the effect of chemical agents on oxygen consumption and the oxygen extraction rate of the joint cells alone; directly and simultaneously measuring the effect of anti-inflammatory drugs on hemodynamic parameters of the joint, and on transsynovial parameters of the joint, such as the permeability of the synovial membrane of a joint, the production of synovial fluid by the joint, and the composition of the synovial fluid of the joint. Each of these methods is useful for evaluating the efficacy of chemical agents on joint inflammation. The methods of the present invention employ a joint preparation which comprises: an isolated joint; a perfusate for perfusating the joint; an inflow conduit for introducing perfusate into the isolated joint; an outflow conduit for receiving perfusate from the isolated joint; means for circulating perfusate through the isolated joint; and oxygenator for oxygenating the perfusate. To quantify the release of a chemical agent, from the synovial cavity of the joint into the vascular system, the chemical agent is injected into the synovial cavity of the isolated joint of the joint preparation. Thereafter, an aliquot of perfusate is withdrawn from the outflow conduit and assayed for presence of the anti-inflammatory drug. Preferably, the amount of drug in the aliquot and the rate of flow of the perfusate from the isolated joint are also measured, so that total amount of the drug which leaks from the synovial cavity is determined.

20 Claims, 2 Drawing Sheets

METHODS FOR EVALUATING EFFICACY OF ANTI-INFLAMMATORY ON DRUGS ON JOINT INFLAMMATION

BACKGROUND

Joint inflammation is one of the most common causes of pain, lameness, and loss of physical activity, not only in humans but in animals, particularly horses. This debilitating condition is marked by edema, redness, heat and pain. If left untreated, joint inflammation also can lead to destruction of the joint synovium and the articular cartilage producing a permanent debilitating condition.

The edema, redness, and pain that occur during inflammation are the result of physiological changes in the joint. For example, the permeability of the synovial membrane increases during inflammation allowing synovial fluid to leak into the tissues of the joint. Alterations in blood flow and pressure in the vascular system of the joint also occur during inflammation. In addition, the metabolic activity of the cells of the joint increases during inflammation. Anti-inflammatory drugs are designed to counter some or all of these physiological changes. Unfortunately, it is not possible to directly and simultaneously measure the effect of anti-inflammatory drugs on the physiological changes at the joint.

It is also difficult to determine the amount of drug that is released from joints. One particularly effective treatment of joint inflammation involves injection of anti-inflammatory drugs directly into the synovial cavity of the afflicted joint, i.e. intra-articular injection. Direct injection results in delivery of a greater concentration of the anti-inflammatory drug directly to the site of inflammation. Anti-inflammatory drugs have side effects or even when present in low concentrations in the systemic circulation. Unfortunately, since the synovial membrane tends to become more permeable during inflammation, significant quantities of the anti-inflammatory drug often enter the bloodstream, and thus the system of the patient. The release of drugs from the synovial cavity during inflammation also reduces the concentration of the anti-inflammatory drugs at the site of inflammation. Unfortunately, one cannot accurately and directly measure the amount of any drug which is released from the synovial cavity into the vascular system following intra-articular injection. Thus, it is also extremely difficult to determine the optimum dose and the dosing schedule for anti-inflammatory drugs that are injected into the synovial cavity.

Accordingly, it would be desirable to have a method for accurately quantifying the release of anti-inflammatory drugs from the synovial cavity to the vascular system of the joint. It would also be desirable to have a method which simultaneously measures the effect of anti-inflammatory drugs on the hemodynamic characteristics of the joint and that allows for co-determination of the effect of the drug on the metabolic activity of the cells of the joint. Such a method would enable one to fully and easily evaluate the efficacy of new anti-inflammatory drugs on the physiological changes that are associated with inflammation.

SUMMARY OF THE INVENTION

The present invention provides novel methods for detecting and quantifying the release of chemical agents, such as anti-inflammatory drugs from the synovial cavity of a joint into the vascular system of the joint. The present invention also provides a novel method for directly measuring the effect of chemical agents on oxygen consumption and the oxygen extraction rate of the joint cells alone. The present invention also provides a novel method for directly and simultaneously measuring the effect of anti-inflammatory drugs on hemodynamic parameters of the joint, such as joint arterial flow and pressure, joint venous flow and pressure, and joint capillary pressure and on transsynovial parameters of the joint, such as the permeability of the synovial membrane of a joint, the production of synovial fluid by the joint, and the composition of the synovial fluid of the joint. Each of these methods is useful for evaluating the efficacy of chemical agents on joint inflammation.

The methods of the present invention employ a joint preparation which comprises: an isolated joint; a perfusate for perfusating the joint; an inflow conduit for introducing perfusate into the isolated joint; an outflow conduit for receiving perfusate from the isolated joint; means for circulating perfusate through the isolated joint; and an oxygenator for oxygenating the perfusate.

In one embodiment, the joint preparation is totally free of a host animal and the oxygenator is an oxygenating device to oxygenate the perfusate and preferably, a pump to recirculate the perfusate through the isolated joint. In the preferred embodiment, the oxygenator is the animal's lungs and the perfusate is circulated by the heart.

In the method for quantifying the release of a chemical agent, such as an anti-inflammatory drug from the synovial cavity of the joint into the vascular system, the chemical agent is injected into the synovial cavity of the isolated joint of the joint preparation. Thereafter, an aliquot of perfusate is withdrawn from the outflow conduit and assayed for presence of the anti-inflammatory drug. Preferably, the amount of drug in the aliquot and the rate of flow of the perfusate from the isolated joint are also measured, so that total amount of the drug which leaks from the synovium is determined.

For determining the oxygen consumption and oxygen extraction rate of the joint, a first aliquot of perfusate is withdrawn from the inflow conduit and a second aliquot of perfusate is withdrawn from the outflow conduit and the temperature of the joint determined. The partial pressure of oxygen in the first and second aliquot is measured using a blood gas analyzer, to determine the arterial partial oxygen pressure and the venous partial oxygen pressure, respectively. At the same time the aliquots are removed, the rate of flow of perfusate into the isolated joint is measured. The hemoglobin content of the perfusate and the hemoglobin saturation of the perfusate are also determined and the isolated joint is weighed using a weight measuring device in contact with the isolated joint. These measurements are used to calculate the amount of oxygen delivered to the joint, the amount of oxygen consumed by the joint and the amount of oxygen extracted from the perfusate by the joint. The measurements are made before and after an anti-inflammatory drug is administered to the isolated joint.

For measuring the effect of anti-inflammatory drugs on the hemodynamic parameters of the joint and the transsynovial parameters, perfusate flow into and out of the joint are measured using a fluid flow measuring device connected to the inflow conduit and outflow conduit, respectively. Arterial pressure and venous pressure are measured using a pressure transducer connected to the inflow conduit and outflow conduit, respectively. The measurements are taken before and after the anti-inflammatory drugs are administered to the joint.

The permeability of the synovial membrane is determined by injecting an indicator which is a compound having a molecular weight that does not normally pass through the synovial membrane, into the synovial cavity and measuring the amount of the indicator present in the perfusate flowing from the joint.

The present invention also relates to the joint preparation itself.

DETAILED DESCRIPTION OF THE INVENTION

Figure 1:
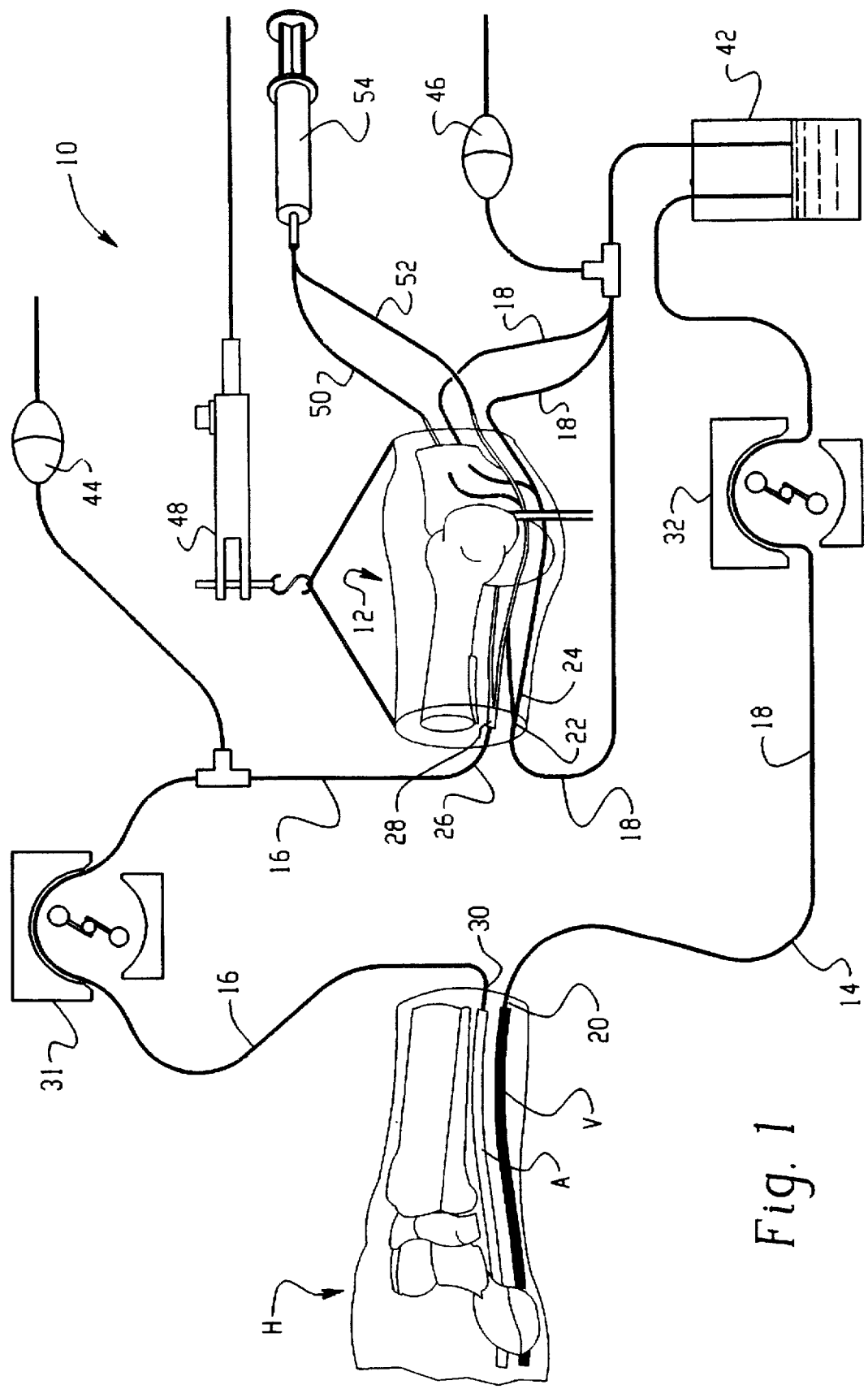
FIG. 1 shows an embodiment of the joint preparation which utilizes the host animal to oxygenate and circulate the perfusate.

The present invention provides novel methods for quantifying the release of anti-inflammatory drugs from the synovial cavity of an isolated joint in a joint preparation into the vascular system of the joint in a joint preparation. The single outflow conduit of the joint preparation receives the perfusate which exits the joint. The perfusate that enters the outflow conduit is substantially all of the perfusate that exits the isolated joint because the isolated joint is free of tendons and muscles which would, if present, remove or absorb the perfusate. In addition, the outflow conduit does not receive any perfusate that does not first pass through the vascular system of the joint. This is due to the fact that the joint preparation lacks any veins that are not part of the vascular system of the joint. Accordingly, the joint preparations of the present invention are especially well-suited for detecting and accurately measuring the release of small quantities of anti-inflammatory drugs from the synovial cavity of a joint into the vascular system of the joint.

In the intact animal, the venous blood exits the joint not only from these multiple locations, such as the muscles. Moreover, in the intact animal peripheral veins feed into the veins of the joint and, therefore, the venous blood of the joint is diluted with blood coming from other sites in the animal beside the joint. Accordingly, very low levels of drugs that leak from the synovial cavity into the vascular system of the joint and into the systemic circulation cannot be detected in the intact animal because of this dilution. Nor can the total amount of anti-inflammatory drugs which is released from the synovial cavity into the vascular system of the animal be determined in the intact animal.

The present invention also provides a method which employs the joint preparation for directly and simultaneously measuring the effect of anti-inflammatory drugs on arterial blood flow and pressure of the joint, venous blood flow and pressure of the joint, and capillary pressure of the joint, hereinafter collectively referred to as "hemodynamic parameters of the joint"; and on synovial fluid production, synovial fluid composition, and synovial membrane permeability, hereinafter collectively referred to as "transsynovial parameters"; and on oxygen delivery to the joint, oxygen consumption and extraction by the cells of the joint, hereinafter collectively referred to as "indicators of cellular metabolic activity in the joint".

Hemodynamic parameters of the joint and transsynovial parameters cannot be measured directly and simultaneously in the intact animal. Moreover, the effect of anti-inflammatory drugs on delivery of oxygen to cells of the joint, the oxygen consumption of the joint cells and the oxygen extraction rate of just joint cells alone cannot be measured in the intact animal. Thus, a method of simultaneously and directly measuring the effect of anti-inflammatory drugs on these physiological parameters is especially useful for evaluating the efficacy of anti-inflammatory drugs on the conditions associated with joint inflammation.

METHODS FOR MEASURING THE EFFECT OF CHEMICAL AGENTS ON THE METABOLIC ACTIVITY OF THE CELLS OF THE JOINT AND ON THE JOINT HEMODYNAMIC PARAMETERS AND THE TRANSSYNOVIAL PARAMETERS

The effect of a chemical agent, particularly an anti-inflammatory drug on hemodynamic parameters, transsynovial parameters, and indicators of cellular metabolic activity in the joint is determined using the joint preparation. The indicators of cellular metabolic activity are measured before and after administration of the drug. The hemodynamic parameters are also measured before and after administration of the drug. For a complete assessment of the efficacy of the anti-inflammatory drug, the values obtained following treatment with the drug are compared to the values obtained in a healthy joint. The values obtained for a healthy joint are shown in Tables 1 and 2.

The effect of inflammatory agents on hemodynamic parameters, transsynovial parameters, and indicators of cellular metabolic activity are also determined using the joint preparation.

Hemodynamic Parameters of the Joint

Perfusate flow into the isolated joint ($Qa_{cir}$) is determined by measuring the rate of flow of perfusate through the inflow conduit. Perfusate flow from the isolated joint ($Qv_{cir}$) is determined by measuring the rate of flow of perfusate through the outflow conduit. One preferred technique is to connect the inflow conduit or outflow conduit to a peristaltic pump which measures and displays fluid flow and pressure of the perfusate within the tubing of the inflow conduits.

A suitable peristaltic pump is the Masterflex Variable Speed Pump from Cole Palmer International.

Joint arterial pressure ($Pa_{cir}$) is determined by measuring the perfusate pressure in the inflow conduit. Joint venous pressure ($Pv_{cir}$) is determined by measuring the perfusate pressure in the outflow conduit. A suitable device for measuring perfusate pressure is a pressure transducer, such as for example, the Spectramed P23XL.

Capillary pressure is measured using the occlusion method which involves clamping off or occluding the veins or arteries associated with the particular capillary bed and measuring the resulting pressure transition. The inflection point between the rapid and slow phase component of the pressure tracing of the clamped veins or arteries represents the capillary pressure. Total vascular resistance of the joint, precapillary resistance and postcapillary resistance of the joint are calculated by dividing the arterial ($Pa_{cir}$)-venous ($Pv_{cir}$), arterial ($Pa_{cir}$)-capillary (Pcap), and capillary (Pcap)-venous pressure gradients, respectively, by blood flow.

Weight of the Isolated Joint

Monitoring the weight of the isolated joint permits determination of hemodynamic and indicators of joint cell metabolic activity, such as oxygen consumption, on a per gram of tissue basis. Monitoring the weight of the isolated joint also permits determination of whether the joint is in an isogravimetric state, i.e. neither gaining weight nor losing weight. Typically, a joint will gain weight if inflamed or lose weight if dehydrated or if inflammation is receding.

The weight of the isolated joint is measured and monitored by attaching the isolated joint to a weight measuring system. A suitable weight measuring system is the FTO3 transducer obtained from Grass Instruments, Quincy, Mass. The FTO3 transducer is attached to the isolated joint via suspended wires attached to the ends of the bone of the isolated joint. For ease of monitoring, the weight measuring system is connected to a physiograph, such as the Grass Model 7D Polygraph which is sold by Grass Instruments, Quincy, Mass.

Determination of Oxygen Delivery, Oxygen Consumption, and Oxygen Extraction Rate of the Cells of the Joint The effect of an anti-inflammatory drug on oxygen delivery, oxygen consumption and oxygen extraction by the cells of the joint is determined by measuring the changes that occur in partial arterial oxygen pressure in the perfusate, hereinafter "$PaO_2$", and partial oxygen pressure in the perfusate flowing from the isolated joint, hereinafter "$PvO_2$" before and after administration of the anti-inflammatory drug. To measure $PaO_2$, an aliquot of perfusate is withdrawn from the artery of the isolated joint or from the inflow conduit using a heparinized syringe. To measure the $PvO_2$, an aliquot of perfusate is withdrawn from the outflow conduit using a separate heparinized syringe. Preferably, each syringe is immediately capped to prevent contamination with air and put on ice to prevent further consumption of oxygen by the cells, such as blood cells, in the perfusate. The $PaO_2$ and $PvO_2$ are then determined using a conventional blood gas analyzer. A suitable gas analyzer is the ABL500 gas analyzer available from Radiometer Copenhagen, Copenhagen, Denmark, which is used according to the manufacturer's instructions. The hemoglobin content, hereinafter "Hb", in the blood cells and hemoglobin saturation, hereinafter "Hbsat", are measured by an OSM3 co-oximeter model available from Radiometer Copenhagen, Copenhagen, Denmark. The tissue temperature, $PaO_2$, $PvO_2$, Hb and Hbsat, plus the arterial blood flow, i.e. $Qa_{cir}$, and weight of the joint at each measurement are used to calculate the oxygen delivery, oxygen consumption by the cells of the joint, and the oxygen extraction rate of the cells of the joint using the following equations:

---

$O_2$ content = Hb × $SaO_2$ × 1.36 (1.39) + Pa $O_2$ × .003 (ml/dl)
A-V $O_2$ difference = C (a − v̄)$O_2$ (ml/dl)
$O_2$ delivery: $CaO_2$ × Q̇ = $CaO_2$ (ml/dl) × 10 dl/L × Q̇ (L/Min) here: $CaO_2$ (ml/dl) × Q̇ (ml/min) divided by weight of prep.
$O_2$ consumption: C (a − v̄) $O_2$ × O /weight
$O_2$ extraction rate: ($CaO_2$ − $C_vO_2$)/$CaO_2$

---

A similar technique is used to measure the partial oxygen pressure of the synovial fluid.

Synovial Fluid Production and Composition

A tube is inserted into the synovial cavity of the isolated joint to collect the synovial fluid for measuring synovial fluid production. Suitable tubes include for example 18 gauge polyethylene flexible tubing. The concentration of total protein in the synovial fluid perfusate fluid and lymph are determined using conventional techniques or assays, such as, for example, the Dye Binding Assay obtained from Bio-Rad Labs, California or by refractometry. The concentration of albumin in the synovial fluid, in the perfusate fluid, and in the lymph are determined using conventional techniques, such as for example electrophoresis.

Protein (total and albumin) is used for calculation estimates of osmotic reflection coefficients synovial fluid, transitional microvascular pressure, and oncotic pressures for plasma, synovial fluid, and lymph. Fluid osmotic reflection coefficients were calculated as 1-Cl.s/Cp where Cl,s is the concentration (g/100 ml) of protein in the lymph or synovial fluid, respectively, and Cp is the concentration of protein in the plasma collected at the same time period. Transitional microvascular pressure for synovial fluid flow (TMPS) was calculated using the formula:

$$TMPs = \pi p - \pi s + Ps \text{ where:}$$

πp is the oncotic pressure in plasma;
πs is the oncotic pressure in synovial fluid; and
Ps is the hydrostatic pressure of the synovial fluid.

Fluid oncotic pressure (π) was estimated by the calculation formula $\pi = 1.4C + 0.22C^2 + 0.005 C^3$.

The presence and concentration of white blood cells in the synovial fluid, which is an indicator of inflammation, is determined using conventional cytological techniques.

Permeability of the Synovial Membrane of the Joint

Following establishment of the isogravimetric state, one or more indicators of permeability are injected into the synovial cavity of the isolated joint of the joint preparation. The indicator that has a molecular weight of at least 40,000 daltons, preferably, a molecular weight of at least 70,000 daltons, that because of its size normally does not pass through the synovial membrane. Examples of compounds having appropriate molecular weights for use as an indicator of permeability include proteins such as albumin or globulins, polysaccharides such as chondroitin sulfate, keratin sulfate, dextrans, and betastarches. For ease of detection the indicators are tagged with a radiolabel or fluorescent label. Preferably, the indicator is inert, i.e., does not chemically interact with the membranes of the joint.

Following injection of the indicator, one or more aliquots of perfusate are periodically withdrawn from the outflow conduit. The concentration of indicator in each aliquot is measured using conventional techniques, such as flow cytometry, spectrophotometry, and chromatography. The rate of flow of the perfusate from the veins of the vascular system of the isolated joint is also measured. A preferred method of measuring perfusate flowing from the isolated joint is to attach a calibrated flow pump to the outflow conduit. The concentration of indicator in the aliquot and the rate of flow of perfusate from the veins of the joint are used to calculate the total amount of indicator which passes through the synovial membrane and into the perfusate during the assay.

MEASURING THE RELEASE OF CHEMICAL AGENTS FROM THE SYNOVIAL CAVITY INTO THE VASCULAR SYSTEM OF THE JOINT

Treatment of joint disease, particularly inflammation, have often involved injecting anti-inflammatory drugs directly into the synovial cavity of an inflamed joint in order to optimize the concentration of the drug at the site of inflammation. Direct synovial injection techniques have also been employed to administer toxic antiflammatory drugs, the rationale being that the host will be exposed to less of the toxic drug by direct injection than by a systemic administration. Since the synovial membrane is not necessarily impermeable to these drugs, toxic quantities of these drugs may still be released into the vascular system, especially when large doses of the drug are injected into the synovial cavity. The extreme difficultly in quantifying the amount of drug released from the synovial cavity, has led to a reluctance to use toxic yet effective anti-inflammatory drugs to treat joint inflammation.

The present invention provides a novel method of measuring the release of chemical agents, preferably anti-inflammatory drugs from the synovial cavity into the vascular system of the joint using the joint preparation. The anti-inflammatory drug is injected into the synovial cavity of the isolated joint. The isolated joint is continuously perfused. Thereafter, an aliquot of perfusate is withdrawn from the outflow conduit and assayed for presence of the anti-inflammatory drug. To quantify the total amount of anti-inflammatory drug released from the synovial cavity into the vascular system per unit time, the concentration of drug in the aliquot and the rate of flow of the perfusate into the outflow conduit are also measured.

The anti-inflammatory drug is administered in a carrier, preferably of the same carrier used in treating patients. The drug is optionally labeled, for example, radiolabeled or fluorescently-labeled for ease of detection. Preferably, the drug is administered in a single dose. The amount of drug administered in a single dose to the joint typically ranges from about 1 to 500 mg, preferably 1–10 mg for potent and toxic drugs to about 100–300 mg for less toxic drugs.

Prior to administration of the drug, an aliquot of perfusate is removed from the outflow conduit for use as a control blank. Following injection of the drug, aliquots of perfusate are removed from the outflow conduit at one or more intervals and the concentration of the drug in the aliquot is determined using conventional techniques, such as fluorospectrophotometry, quantitative immunoassays, high performance liquid chromatography, gas chromatography or other chromatographic techniques.

To determine the amount of anti-inflammatory drug released per unit of time after injection, the rate of flow of the perfusate from the isolated joint of the joint preparation, i.e. the venous flow, into the outflow conduit is measured. The rate of release of the anti-inflammatory drug from the joint is useful for determining the optimum dose of the drug, i.e. a dose which is both effective at reducing inflammation and yet is not substantially released into the system of the host animal.

JOINT PREPARATIONS

The joint preparation comprises the isolated joint, a perfusate for perfusating the isolated joint, an inflow conduit for introducing perfusate into the isolated joint, an outflow conduit for receiving perfusate from the isolated joint, means for circulating perfusate through the isolated joint, and an oxygenator for oxygenating the perfusate.

The isolated joint comprises: the condyle of each of the two bones of the joint, each bone is transected at a point above the condyle region of the bone and preferably below the diaphysis of the bone; cartilage disposed along the edge of the condyle regions of the bones; a synovium comprising a synovial membrane which defines a synovial cavity; and the joint vascular system comprising transected arteries and transected veins connected to the capillaries which feed the cartilage, synovium, and condyle regions of the bones. Preferably the isolated joint is free of tendons and muscles, since such tissue removes perfusate and prevents the removed perfusate from reaching the outflow conduit. Preferably the isolated joint further comprises skin surrounding both the bones and vasculature of the isolated joint.

In the first embodiment, the joint preparation comprises an isolated joint in which the vascular system of the isolated joint is connected to the vascular system of the host animal via tubing. Optionally, such embodiment further comprises intact nerves which innervate the joint. In the second alternative embodiment, the isolated joint is not connected to the host animal, that is, the joint preparation is completely free of the animal.

In both embodiments the preferred joint is the equine metacarpophalangeal (MCP) joint, although other joints are also suitable. The MCP joint is the second most common joint affected with arthritis in horses and, thus, is an especially suitable joint for measuring the effects of anti-inflammatory drugs on the inflammation. Moreover equine osteoarthritis is histologically similar to human osteoarthritis and has been extensively studied. Thus, the MCP joint is a good model for evaluating the efficacy and release of anti-inflammatory drugs that are developed for veterinary use and for human use.

First Embodiment

FIG. 1 shows the preferred embodiment of the first embodiment of the joint preparation, shown generally as 10, in which the isolated joint 12 is connected to the host animal. Joint preparation 10 comprises isolated joint 12, a perfusate for perfusing the isolated joint 12, inflow conduit 16, and outflow conduit 18. Outflow conduit 18 has a first end 20 which is connected to at least one vein V of the host animal H. Preferably, outflow conduit 18 has a second end 22 connected to at least one vein 24 of the isolated joint 12. Inflow conduit 16 has a first end 26 connected to at least one artery 28 of isolated joint 12 and second end 30 connected to at least one artery A of the host animal H, thereby permitting recirculation of the perfusate 14 from the outflow conduit 18, through the vascular systems of the host animal H and the isolated joint 12. Preferably, inflow conduit 16 is in fluid communication with the artery 28 leading into the isolated joint 12 above the branch point of the artery 28.

Although the heart of the host animal can be used to pump the perfusate through the isolated joint 12, it is preferred that the joint preparation also comprise a first pump 31 connected to the inflow conduit 16 for controlling the rate of flow of the perfusate 14 into the isolated joint 12 and a second pump 32 connected to outflow conduit 18 for pumping the perfusate 14 from the outflow conduit 18 and into the vein V of the host animal H. The lungs of the host animal oxygenate the blood. Optionally, the joint preparation 10 also comprises an intact nerve of the host animal which innervates the isolated joint 12.

A reservoir 42 for storing the perfusate is fluidly connected to the outflow conduit 18.

Preferably, but optionally, the joint preparation 10 comprises a fluid flow measuring device in contact with the inflow conduit 16 for measuring perfusate 14 flow into isolated joint 12. Preferably, this function is contained in pump 31. Preferably, but optionally, the joint preparation comprises a pressure transducer 44 in contact with conduit 16 for measuring arterial pressure. Preferably, but optionally, the joint preparation 10 comprises a fluid flow measuring device pressure transducer 46 in contact with the outflow conduit 18 for measuring of the rate of flow of the perfusate 14 out of the isolated joint 12, venous pressure, respectively. Suitable fluid flow measuring devices include the Doppler flow probe available from Transonics, Ithaca, N.Y., and the Electromagnetic flow probe available from Caroling Instruments, and the Masterspeed variable flow pump. Examples of a pressure transducer which are suitable for measuring arterial pressure and venous pressure include a Spectramed P23XL. Preferably the measuring device 44 and 46 are connected to a recording device, such as a physiograph, for recording and displaying the measurements made by the measuring devices 44 and 46.

The joint preparation 10 optionally but preferably comprises a weight measuring system 48 connected to the isolated joint 12 to weigh the isolated joint 12. The weight measuring system 48 is used to determine isogravometric state and to determine the oxygen consumption and an oxygen extraction rate for the cells of the joint.

Preferably, withdrawal ports 50 and 52 are in fluid communication with the portion of the artery 28 which continues beyond the isolated joint 12, such withdrawal ports 50 and 52 are connected to reference syringe 54. Reference syringe 54 permits withdrawal of perfusate sample directly from the artery 28 of the isolated joint 12.

Second Embodiment

Figure 2:
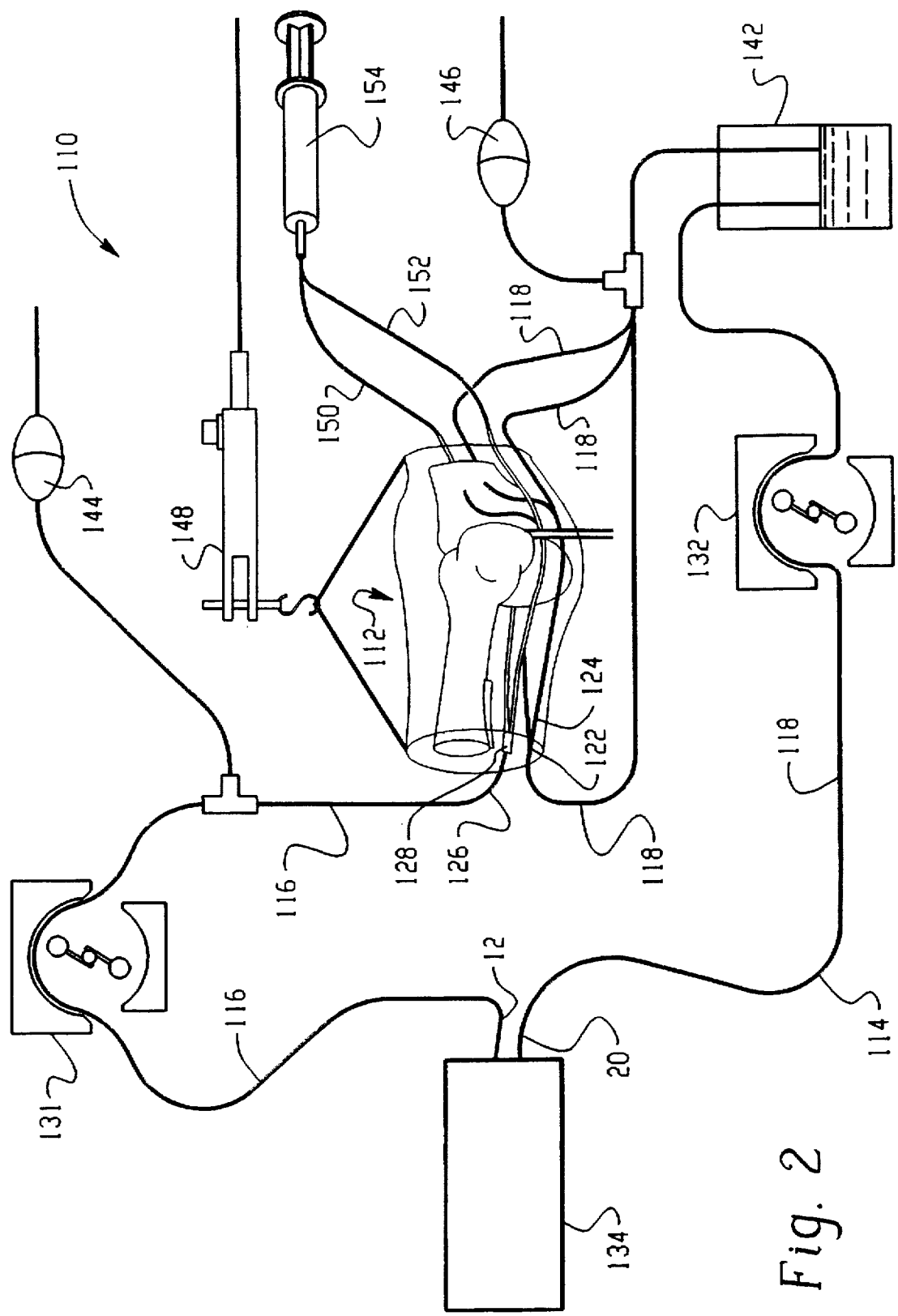
FIG. 2 shows an embodiment of the joint preparation which utilizes an oxygenating device to oxygenate and circulate the perfusate.

FIG. 2 shows the preferred embodiment of the second embodiment of the joint preparation, shown generally as 110, in which the isolated joint 112 is free of the host animal. Joint preparation 110 comprises isolated joint 112, a perfusate for perfusing the isolated joint 112, inflow conduit 116, and outflow conduit 118. Outflow conduit 118 has a first end 120. Preferably, outflow conduit 118 has a second end 122 connected to at least one vein 124 of the isolated joint 112. Inflow conduit 116 has a first end 126 connected to at least one artery 128 of isolated joint 112 and second end 130 in fluid communication with first end 120 of outflow conduit 118, thereby permitting recirculation of the perfusate 114 from the outflow conduit 118, through the inflow conduit 116 and the isolated joint 112. Preferably, inflow conduit 116 is in fluid communication with the artery 128 leading into the isolated joint 112 above the branch point of the artery 128. A reservoir 142 for storing the perfusate is fluidly connected to the outflow conduit 118.

The joint preparation also preferably comprises a first pump 131 connected to the inflow conduit 116 for pumping and controlling the rate of flow of the perfusate 114 into the isolated joint 112 and a second pump 132 connected to outflow conduit 118 for pumping the perfusate 114 from the outflow conduit 118 to oxygenator 132.

Preferably, the oxygenator oxygenates and thermally regulates the perfusate; suitable oxygenators are performed by bypass machines composed of an oxygenation pump and polyethylene tubing and silastic tubing such as made by Travenol Lab, Inc., by Sarns, Ann Arbor, Mich.

Preferably, but optionally, the joint preparation 110 comprises a fluid flow measuring device in contact with the inflow conduit 116 for measuring perfusate 114 flow into isolated joint 112. Preferably, this function is contained in pump 131. Preferably, but optionally, the joint preparation comprises a pressure transducer 144 in contact with conduit 116 for measuring arterial pressure. Preferably, but optionally, the joint preparation 110 comprises a fluid flow measuring device pressure transducer 146 in contact with the outflow conduit 118 for measuring of the rate of flow of the perfusate 114 out of the isolated joint 112, venous pressure, respectively. Suitable fluid flow measuring devices include the Doppler flow probe available from Transonics, Ithaca, N.Y., and the Electromagnetic flow probe available from Caroling Instruments, and the Masterspeed variable flow pump. Examples of a pressure transducer which are suitable for measuring arterial pressure and venous pressure include a Spectramed P23XL. Preferably the measuring device 144 and 146 are connected to a recording device, such as a physiograph, for recording and displaying the measurements made by the measuring devices 144 and 146.

The joint preparation 110 optionally comprises a weight measuring system 148 connected to the isolated joint 112 to weigh the isolated joint 112. The weight measuring system 148 is used to determine isogravometric state and to determine the oxygen consumption and an oxygen extraction rate for the cells of the joint.

Preferably, withdrawal ports 150 and 152 are in fluid communication with the portion of the artery 128 which continues beyond the isolated joint 112, such withdrawal ports 150 and 152 are connected to reference syringe 154. Reference syringe 154 permits withdrawal of perfusate sample directly from the artery 128 of the isolated joint 112.

Perfusate

The perfusate is an isotonic solution that comprises an anti-coagulant, preferably heparin. The perfusate maintains the isolated joint in a state that is physiologically responsive to manipulations in arterial pressure or venous pressure, preferably for at least 30 minutes, more preferably for at least four hours, after construction of the joint preparation. Preferably, the perfusate has a pH of between 7.35 and 7.45. Preferably, the perfusate has an osmolarity of between 295 mOsm and 310 mOsm. Suitable examples of perfusate include, for example, balanced salt solutions, stroma-free hemoglobin solutions, colloids, and blood.

Inflow and Outflow Conduits

The inflow conduit and outflow conduit contain the perfusate, and preferably comprise tubing. The inflow and outflow conduits are preferably a flexible synthetic tubing, more preferably, silicone or polyethylene. Preferably, the tubing is silicone; suitable silicone tubing is available from Baxter Health Care, McGraw Park, Ill.

The silicone tubing is rinsed internally with 1 ml of heparinized saline (10,000 units/ml) and connected to the flexible plastic tubing of the pump system by inserting the silicone tubing into the internal diameter of the plastic tubing of the pump and securing the two tubes with a plastic circumferential clamp. Suitable flexible plastic tubing for use in the pump includes, for example, Tygon Flexible Plastic Tubing by Norton, Akron, Ohio.

A pump which is suitable for pumping perfusate is a peristaltic pump through which the tubing of the inflow conduit or outflow conduit is looped.

Construction of the Joint Preparation

The MCP joints were isolated from horses donated and designated for euthanasia for other than skeletomuscular reasons. All horses were managed in accordance with the Animal Care and Use guidelines.

Prior to isolation of the MCP joint from the forelimb, the horse was sedated with xylazine (0.5 mg/kg, iv), and anesthesia was induced with glyceryl guaiacolate (to effect) followed by sodium thiopental (2 mg/kg, iv). Anesthesia was maintained with sodium pentobarbital (5–15 mg/kg/hr to effect) and controlled mechanical ventilation with 100% oxygen was used throughout the procedure. The horse was positioned in lateral recumbency, and anesthesia was monitored by continuous display of direct systemic arterial blood pressure measurement (mean and systolic), hourly cardiac output measurement using a thermodilution technique, and intermittent arterial blood gas measurement. Mean systemic arterial blood pressure was maintained at $\geq 70$ mmHg, and ventilation was adjusted to maintain $PaO_2 \geq 150$ mm Hg and $PaO_2 \leq 55$ mmHg. Heparin (50,000 units IV) was administered into the systemic circulation of the horse prior to isolation of the joint, and at every 90 minutes following isolation.

Following administration of the anesthetic and heparin, the inflow conduit, an arterial cannula, was placed in the median artery of the horse proximal to the anticipated site of joint isolation and also placed in the medial palmar artery, which is a component of the arterial system of the MCP joint. The inflow conduit was polyethylene tubing PE240 obtained from Fischer Company. The inflow conduit was positioned in a peristaltic pump, a Masterflex Variable Speed Pump by Cole Parmer International, Chicago, Ill., which allows for control of arterial flow into the joint. The inflow conduit was also connected via tubing to a pressure transducer for continuous monitoring of arterial pressure on a VR-12 physiograph by Honeywell Corporation. The outflow conduit was also connected to the veins of the joint and to the median vein of the horse. The second end of the outflow conduit comprises three venous cannulas that were attached to the medial palmar, lateral, and medial palmar digital veins of the joint for collection of perfusate from the joint, and a first end which is a cannula that was connected to the median vein of the horse for recirculation of the perfusate back into the host animal. The outflow conduit is also comprised of a reservoir for storage of the perfusate, which was the heparinized blood pumped into the joint preparation from the horse. The reservoir was connected to the tubing which forms the first set of venous cannulas and to the tubing which forms the second venous cannula. The first set of venous cannulas of the outflow conduit was in fluid communication with Spectramed P23XL transducer for continuous monitoring of venous pressure on a VR-12 Honeywell Corporation Physiograph. The tubing which formed the second venous cannula of the outflow conduit was connected to the tubing of a peristaltic pump for monitoring the rate of flow from the isolated joint.

Following attachment of the inflow and outflow conduits, all soft tissue and bone at the level of the distal metacarpus was transected and the proximal interphalangeal digit, i.e. the joint, was dislocated from the limb.

Following dislocation, the joint was attached to a FT03 transducer from Grass Instruments, Quincy, Mass., connected to a physiograph for continuous display of the weight of the joint. Following dislocation of the joint, a distended lymphatic vessel visible around the catheterized lateral palmar artery was cannulated with a fine 26 g catheter for collection of lymph. The catheter was capped between collections. A 22 g intra-articular catheter was placed in the dorsal pouch of the MCP joint and attached to a shielded photoelectric cell drop counter. The catheter was connected to maintain atmospheric intra-articular pressure and to determine trans-synovial fluid flow (Qs). In this system, 16.5 drops was approximately 1 ml of fluid.

Simultaneous Measurement of Hemodynamic Parameters and Trans-synovial Parameters in a Normal Joint Arterial pressure ($Pa_{cir}$) in the inflow conduit was measured using a calibrated transducer, a Spectramed P23XL transducer, and then was set at 150 mmHg by adjustment of flow in pump, and venous pressure (Pvcir) in the outflow conduit was measured using a calibrated transducer, a Spectramed P23XL transducer, and was adjusted using a clamp and initially maintained at 10 mmHg.

After 25 minutes of equilibration in the isogravimetric state, five minutes were allotted for measuring perfusate flowing into the isolated joint ($Qa_{cir}$), perfusate flowing from the isolated joint (Qvcir), synovial flow (Qs) and lymphatic flow (Q1). Capillary pressure was also determined at isogravimetric state and pre- and post capillary resistance and pre- and post capillary resistance ratios calculated. These values are shown in Table 2.

Responsiveness of the Joint Preparation to Manipulations of Arterial and Venous Pressure Example A Perfusate pressure in the inflow conduit was adjusted to 100, 150, 200 and 250 mmHg for 30 minutes using the peristaltic pump and circuit arterial pressure ($Pa_{cir}$), circuit arterial ($Qa_{cir}$) and venous ($Qv_{cir}$) flow, synovial fluid production (Qs), lymph production (Q1) and weight changes, that is vascular and tissue compliance were recorded in the last 5 minutes of the 30 minutes at each pressure. Pacir was returned to the isogravimetric state for 30 minutes before venous pressure manipulations ($Pv_{cir}$). Measurements, including tissue blood flow utilizing a colored microsphere technique and capillary pressure (Pcap) were recorded in the last 5 minutes of the isogravimetric condition. Capillary pressure was measured using the venous occlusion method. $Pv_{cir}$ was adjusted to 20 and 40 mmHg and measurements made as described above. These values are shown in Table 1.

To establish that all regions of the isolated joint of the joint preparation were perfused, synovial tissue blood flow in the joint preparation was continually measured using a colored microsphere technique according to Kowalik, P., et al., "Measurement of Regional Myocardial Blood Flow with Multiple Colored Microspheres," *Circulation* 83:974–982, 1991, which is fully incorporated by reference herein, except that synovial membrane blood flow was determined by injection of the microspheres into the median palmar artery. The number of microspheres injected was $3 \times 10^6$ or $6 \times 10^6$. Blue, red or yellow colored Dye-Track colored microspheres obtained from Triton Technology, Inc. were injected in the inflow arterial line and a reference arterial blood sample was withdrawn from the medial palmar digital artery at a rate of 4.94 ml/min for 1 minute. Subsequently, tissue specimens and reference flood samples were digested in KOH and filtered on a 8 µm pore size polyester filter. Dimethylformamide was added to release the dye from the microspheres. Dye concentration was measured by spectrophotometry using a matrix kn version technique for resolution of composite spectra when multiple colors are used. Blood flow was expressed in ml/min/g of tissue. These values are also shown in Table 1.

After 3.5 hours, the isolated joint of the joint preparation was injected with Evans blue-albumin for gross visual inspection of the articular cartilage of the isolated joint which revealed normal articular cartilage as expected.

TABLE 1

| | Pre-prep baseline | Post-prep baseline |
|---|---|---|
| Cardiac output (L/min/kg) | 0.078 ± 0.011 | 0.065 ± 0.009 |
| Mean Arterial Pressure (mmHg) | 130.67 ± 18.23 | 123.86 ± 11.02 |
| Systolic Arterial Pressure (mmHg) | 160.83 ± 22.17 | 152.0 ± 14.24 |
| Arterial Blood Gas | | |
| (PaO2) | 422.66 ± 36.86 | 461.63 ± 35.3 |
| (PaCO2) | 40.48 ± 2.66 | 37.4 ± 3.38 |
| Joint Blood Flow (ml/min) | 68 ± 21.13 | 37.17 ± 13.65 |
| Joint Arterial Pressure (mmHg) | 149.47 ± 12.74 | 133.57 ± 9.07 |
| Joint Venous Pressure (mmHg) | 20.0 ± 0 | 10.5 ± 3.81 |
| Synovium Blood Flow (ml/min/g) | | |
| dorsal | 0.078 ± 0.047 | 0.058 ± 0.009 |
| palmar | 0.067 ± 0.034 | 0.261 ± 0.118 |
| mean | 0.073 ± 0.006 | 0.160 ± 0.102 |
| Joint Resistance (Rt) mmHg/ml | 2.27 ± 0.51 | 6.41 ± 2.62 |

TABLE 1-continued

| | | | |
|---|---|---|---|
| Prep weight gain (g) | — | — | |
| Synovial Fluid Production (drops/min) | — | — | |
| Vascular Compliance (ml/mmHg) | | | |
| Tissue compliance (ml/mmHg) | | | |

| | Pa 100 (mmHg) | Pa 150 (mmHg) | Pa 200 (mmHg) |
|---|---|---|---|
| Cardiac output (L/min/kg) | 0.068 ± 0.011 | 0.056 ± 0.004 | 0.055 ± 0.005 |
| Mean Arterial Pressure (mmHg) | 135.75 ± 14.00 | 105.5 ± 20.65 | 127.67 ± 11.2 |
| Systolic Arterial Pressure (mmHg) | 164.00 ± 17.40 | 160.67 ± 12.51 | 157.17 ± 12.4 |
| Arterial Blood Gas | | | |
| (PaO2) | 395.8 ± 0 | | |
| (PaCO2) | 43 ± 0 | | |
| Joint Blood Flow (ml/min) | 11.0 ± 4.08 | 14.8 ± 5.23 | 24.67 ± 7.05 |
| Joint Arterial Pressure (mmHg) | 108 ± 5.03 | 154.83 ± 2.57 | 201.67 ± 22.01 |
| Joint Venous Pressure (mmHg) | 7.33 ± 1.33 | 7.0 ± 1.33 | 7.83 ± 2.26 |
| Synovium Blood Flow (ml/min/g) | | | |
| dorsal | — | — | — |
| palmar | — | — | — |
| mean | — | — | — |
| Joint Resistance (Rt) mmHg/ml | 12.61 ± 5.67 | 17.78 ± 5.4 | 11.53 ± 2.74 |
| Prep weight gain (g) | 4.33 ± 3.85 | 4.0 ± 2.58 | 16.0 ± 7.32 |
| Synovial Fluid Production (drops/min) | 1.67 ± 0.67 | 4.63 ± 1.42 | 4.08 ± 2.37 |
| Vascular Compliance (ml/mmHg) | 0.042 ± 0.002 | 0.004 ± 0.001 | 0.008 ± 0.002 |
| Tissue compliance (ml/mmHg) | | 0.0114 ± 0.00 | 0.053 ± 0.011 |

| | Pa 250 (mmHg) | Pa 120 (mmHg) |
|---|---|---|
| Cardiac output (L/min/kg) | 0.056 ± 0.004 | 0.05 ± 0.003 |
| Mean Arterial Pressure (mmHg) | 124.0 ± 11.7 | 132 ± 9.38 |
| Systolic Arterial Pressure (mmHg) | 151.5 ± 16.6 | 181.0 ± 14.22 |
| Arterial Blood Gas | | |
| (PaO2) | 439.7 ± 0 | 359.5 ± 0 |
| (PaCO2) | 48.1 ± 0 | 54.8 ± 0 |
| Joint Blood Flow (ml/min) | 46.83 ± 16.95 | 16.33 ± 5.41 |
| Joint Arterial Pressure (mmHg) | 249.0 ± 1 | 121.5 ± 9.49 |
| Joint Venous Pressure (mmHg) | 7.0 ± 1.86 | 9.0 ± 2.90 |
| Synovium Blood Flow (ml/min/g) | | |
| dorsal | — | 0.049 ± 0.03 |
| palmar | — | 0.048 ± 0.014 |
| mean | — | 0.049 ± 0.001 |
| Joint Resistance (Rt) mmHg/ml | 10.89 ± 3.54 | 13.09 ± 4.27 |
| Prep weight gain (g) | 23.67 ± 8.40 | 18.0 ± 9.17 |
| Synovial Fluid Production (drops/min) | 28.57 ± 13.6 | 5.28 ± 2.44 |
| Vascular Compliance (ml/mmHg) | 0.010 ± 0.003 | 0.003 ± 0.001 |
| Tissue compliance (ml/mmHg) | 0.074 ± 0.016 | 0.025 ± 0.007 |

| | Pv 20 (mmkHg) | Pv 40 (mmHg) |
|---|---|---|
| Cardiac output (L/min/kg) | 0.049 ± 0.004 | 0.0451 ± 0.004 |
| Mean Arterial Pressure (mmHg) | 121.33 ± 10.28 | 112.5 ± 10.27 |
| Systolic Arterial Pressure (mmHg) | 149.17 ± 14.32 | 142.0 ± 13.35 |
| Arterial Blood Gas | | |
| (PaO2) | | |
| (PaCO2) | | |
| Joint Blood Flow (ml/min) | 20.42 ± 7.50 | 20.42 ± 6.93 |
| Joint Arterial Pressure (mmHg) | 164 ± 18.66 | 167.17 ± 16.58 |
| Joint Venous Pressure (mmHg) | 20.0 ± 0.00 | 40.0 ± 0.00 |
| Synovium Blood Flow (ml/min/g) | | |
| dorsal | — | — |
| palmar | — | — |
| mean | — | — |
| Joint Resistance (Rt) mmHg/ml | 17.34 ± 6.66 | 13.35 ± 5.31 |
| Prep weight gain (g) | 16.8 ± 4.54 | 12.83 ± 5.65 |
| Synovial Fluid Production (drops/min) | 8.73 ± 4.74 | 14.74 ± 10.45 |
| Vascular Compliance (ml/mmHg) | 0.061 ± 0.033 | 0.039 ± 0.013 |
| Tissue compliance (ml/mmHg) | 0.02 ± 0.004 | 0.029 ± 0.010 |

TABLE 2

| Measurements and Calculations | Values Obtained |
|---|---|
| Joint Arterial Pressure ($Pa_{cir}$ (mmHg) | 121.5 ± 9.49 |
| Joint Venous Pressure ($PV_{cir}$ mmHg) | 9.0 ± 2.90 |
| Joint Capillary Pressure (Pcap mmHg) | 22.60 ± 4.07 |
| Joint Resistance (Rt mmHg/ml) | 13.09 ± 4.27 |
| Joint Arterial Resistance (Rpre mmHg/ml) | 9.55 ± 3.66 |
| Joint Venous Resistance (R post mmHg/ml) | 0.71 ± 0.38 |
| Pre- to post- resistance ratio | 13.45 |
| Contribution R pre (%) | 72.96 |
| Contribution R post (%) | 5.42 |
| Osmotic Reflection Coefficient (lymph n = 1) | |
| Total Protein | 0.69 ± 0 |
| Albumin | 0.79 ± 0 |
| Osmotic Reflection Coefficient (synovial fluid) | |
| Total Protein | 0.31 ± 0.12 |
| Albumin | 0.31 ± 0.14 |
| Oncotic Pressure Synovial Fluid ($\pi s$) mmHg | 7.82 ± 2.9 |
| Oncotic Pressure Plasma ($\pi s$) mmHg | 13.31 ± 3.7 |
| Oncotic Pressure Tissue ($\pi s$) mmHg | 2.82 ± 0 |
| Transitional Microvascular Pressure Synovial Fluid (mmHg) | 5.48 ± 2.3 |
| Transitional Microvascular Pressure Lymph (mmHg) | 2.82 ± 0 |
| Synovial Fluid Production (drops/min) | 5.28 ± 2.44 |
| Vascular Compliance (ml/mmHg) | 0.003 ± 0.001 |
| Tissue Compliance (ml/mmHg) | 0.025 ± 0.007 |

As shown in Table 1, synovial tissue blood flow was similar before, immediately after and at 3.5 hours after joint isolation indicating that the joint preparation maintains flow to all parts of the synovium.

Synovial fluid production and trans-fluid flow, i.e. synovium weight gain, increased when the arterial pressures were increased to a value greater than 200 mmHg, demonstrating a threshold phenomenon for the joint. Transsynovial flow occurred in preference to lymph flow due to the high hydraulic conductance and permeability of synovial tissue. Vascular compliance in the joint was low, an overall mean 0.005, but increased markedly (overall mean 0.08) when venous pressure was increased. Vascular and tissue compliance both increased to peak values of 0.01 and 0.074, respectively, with increased arterial pressure.

These results verified that the isolated joint of the joint preparation possesses the response characteristics of the joint in an intact animal for at least five hours after isolation and therefore suitable is similar to an in vivo joint evaluating the efficacy of anti-inflammatory drugs on joint inflammation. Thus, the isolated joint preparation permits simultaneous and direct measurements of trans-synovial parameters and hemodynamic parameters which is not possible in the intact animal.

The values shown in Tables 1 and 2 represent the values obtained in a non-inflamed joint and provide a context for determining the extent to which anti-inflammatory drugs affect these physiological parameters in an inflamed joint. Measuring the Effect of an Inflammatory Agent on Joint Physiological Parameters and Measuring the Release of an Anti-inflammatory Agent from the Synovial Cavity of Normal and Inflamed Joints.

The effect of the inflammatory agent, interleukin 1 on oxygen delivery, oxygen consumption, and the oxygen extraction rate of the cells of a single isolated joint were determined using joint preparations that were connected to the vascular system of a host animal. The effect of interleukin 1 on the release from the joint synovial cavities into the joint tissues of an indicator of synovial membrane permeability was also evaluated. The indicator of permeability was Evans blue albumin which naturally fluoresces red under light and can be seen in histological sections. Evans blue albumin has a molecular weight of 68,000 daltons.

In addition, the release of dextran, an anti-inflammatory drug, from the synovial cavity into the vascular system of inflamed and normal joints was also quantified using the joint preparations. Dextran had a molecular weight of 144,000 daltons.

To ensure that all regions of the joints were constantly being perfused during the six hour evaluations, blood flow to the synovial membrane in the isolated joint of each joint preparation was determined with colored microspheres immediately and one hour after isolation, and at 5.5 hours after isolation.

EXAMPLE 1

Innervated Joints Treated with Interleukin 1

A sterile saline solution containing 0.35 ng of II-1B per kg of animal was injected into each isolated innervated joint of six joint preparations after establishment of the isogravimetric state, which was approximately 30 minutes, after dislocation of the MCP joint from the forelimb.

The rate of flow of the perfusate flow in the inflow and outflow conduits were measured using calibrated peristaltic pumps with a digital readout. Arterial pressure and venous pressure were measured using pressure transducers connected to the inflow and outflow conduits, respectively, and weight of the joints in each of the six joint preparations were simultaneously and continuously measured. A 2 ml aliquot of perfusate was collected hourly from the inflow conduit and outflow conduit of each joint preparation for measurement of blood gases in perfusate flowing into and out of the isolated joint using a blood gas analyzer, such as the ABL 500 and measuring the hemoglobin and hemoglobin saturation using a co-oximeter such as the OSM3, both made by Radiometer—Copenhagen. The extent of oxygen delivery to the tissues of joint, the amount of oxygen consumed by the cells of the joint, and the ability of these cells to extract oxygen from the perfusate were determined from the blood gas perfusate flow rate, the weight of the isolated joint, and $PaO_2$ and $RiO_2$ hemoglobin values. The values for oxygen delivery, oxygen consumption, and oxygen rate of extraction are shown in Table 3.

Example 1 A. To measure the release of dextran from joints of Example 1 which were inflamed as the result of treatment with interleukin 1, a 2 ml aliquot of a saline solution containing FITC-dextran from Sigma Chemical company was injected into the synovial cavity of each joint in the six joint preparations. A 2 ml aliquot of heparinized blood was withdrawn from the outflow conduit at two minute intervals for thirty minutes following injection of the FITC-dextran. FITC-dextran concentration in the perfusate coming from the isolated joint was quantified by fluorospectrophotometry using a 485 nm excitation wavelength and 530 nm emission wavelength. These values are displayed in Table 4. Simultaneously, perfusate flow from the veins of the isolated joint was measured using the calibrated, digital read-out, peristaltic pump which was connected to the tubing of the outflow conduit. FITC-dextran concentration and perfusate flowing from the isolated joint were used to determine the total amount of FITC-dextran released by each joint into the perfusate flowing from the isolated joint during each time interval. These values are also displayed in Table 4.

Example B. To evaluate the permeability of the synovial membrane of joints that had been treated with interleukin 1, a 2 ml aliquot of Evans-blue albumin composed of Evans Blue Dye, Bovine Serum Albumin and saline, was injected into the synovial cavity of each joint in the six joint preparations at 5.5 hours after injection of the interleukin 1. At thirty minutes following injection of the Evans-blue albumin the joint preparations were disassembled. The synovium was then removed from the joint and sectioned. The depth and distribution of the Evans-blue albumin in the synovium was determined by fluorescent microscopy of the synovium histological sections and Cytofluorescence Measurement system 2330/2350 for quantifying the amount of Evans-blue albumin released from the synovial cavity.

EXAMPLE 2

Denervated Joints Treated with Interleukin 1

Joints were prepared as in example 1 except that the medical and lateral palmer nerve were transected to provide a denervated isolated joint preparation which was then treated as in example 1.

Example 2a. The joint preparations of example 2 were treated as described in example 1a to measure the release of dextran from the isolated joints of these joint preparations.

Example 2b. The joint preparations of example 2 were treated as described in example 1b to evaluate the permeability of the synovial membrane of the isolated joints in the joint preparations of example 2.

EXAMPLE 3

Non-inflamed Innervated Joints

The rate of flow of perfusate in the inflow and outflow conduit and arterial and venous pressures, and the weight of the innervated, isolated joints in each of six joint preparations were continuously measured as described in example 1. Blood gases in the perfusate flowing into and out of the isolated joint were also collected hourly from each of the joint preparations as described in example 1. The extent of oxygen delivery to the tissues of joint, the amount of oxygen consumed by the cells of the joint, and the ability of these cells to extract oxygen from the perfusate were determined from the perfusate flow rate, the weight of the isolated joint, the blood gas values and the hemoglobin values. The values for oxygen delivery, oxygen consumption, and oxygen rate of extraction are shown in Table 3.

Example 3A. To measure the release of dextran from innervated, isolated joints that were not inflamed as the result of treatment with interleukin 1, a 2 ml aliquot of a saline solution containing FITC-dextran from Sigma Chemical company was injected into the synovial cavity of each joint in the six joint preparations of example 3. The release of dextran from the synovial cavity of the joints of the joint preparations of example 3 was then measured as described in Example 1A.

Example 3B. To evaluate the permeability of the synovial membrane of joints that had not been treated with interleukin 1, a 2 ml aliquot of Evans-blue albumin composed of Evans Blue Dye, Bovine Serum Albumin and saline, was injected into the synovial cavity of each joint in the six joint preparations at 5.5 hours after establishment of the isogravimetric state. The joint preparations of example 3 were then treated as described in example 1B.

EXAMPLE 4

Non-inflamed Denervated Joints

Joints were prepared as in example 3 except that the medial and lateral palmer nerve was transected to provide a denervated isolated joint preparation which was then treated as in example 1.

Example 4a. The joint preparations of example 4 were treated as described in example 3a to measure the release of dextran from the denervated, isolated joints that had not received interleukin 1.

Example 4b. The joint preparations of example 4 were treated as described in example 3b to evaluate the permeability of the synovial membrane of the denervated, isolated joints that had not received interleukin 1.

As determined by the microsphere technique, blood flow to the synovial membrane of all the isolated joints of the above examples was lowest after isolation, but subsequently increased and was not different at one hour than at six hours. These results indicate that there was adequate and similar blood flow to all regions of the joints which were components of the joint preparations of the above examples.

TABLE 3

EFFECT OF INTERLEUKEN
OXYGEN DELIVERY $DO_2$, OXYGEN CONSUMPTION AND OXYGEN EXTRACTION RATE IN ml/min/g OF TISSUE OF THE CELLS OF THE ISOLATED JOINTS IN EXAMPLES 1–4

| Time (Hours) | $DO_2$ | $VO_2$ | $O_2ER$ | $DO_2$ | $VO_2$ | $O_2ER$ |
|---|---|---|---|---|---|---|
| | EXAMPLE 1 | | | EXAMPLE 2 | | |
| 0 | 0.284 | 0.017 | 0.072 | 0.420 | 0.136 | 0.034 |
| 1 | 0.288 | 0.017 | 0.088 | 0.465 | 0.044 | 0.97 |
| 2 | 0.300 | 0.023 | 0.973 | 0.614 | 0.041 | 0.056 |
| 3 | 0.288 | 0.029 | 0.140 | 0.744 | 0.038 | 0.053 |
| 4 | 0.477 | 0.037 | 0.087 | 0.856 | 0.038 | 0.047 |
| 5 | 0.619 | 0.049 | 0.098 | 0.805 | 0.033 | 0.046 |
| 6 | 0.643 | 0.051 | 0.098 | 0.874 | 0.039 | 0.054 |
| | EXAMPLE 3 | | | EXAMPLE 4 | | |
| 0 | 0.338 | 0.008 | 0.051 | 0.200 | 0.010 | 0.052 |
| 1 | 0.401 | 0.009 | 0.049 | 0.26 | 0.014 | 0.044 |
| 2 | 0.398 | 0.013 | 0.061 | 0.293 | 0.018 | 0.056 |
| 3 | 0.424 | 0.018 | 0.066 | .0322 | 0.015 | 0.050 |
| 4 | 0.460 | 0.019 | 0.102 | 0.518 | 0.024 | 0.048 |
| 5 | 0.474 | 0.019 | 0.089 | 0.347 | 0.020 | 0.081 |
| 6 | 0.579 | 0.09 | 0.086 | 0.657 | 0.018 | 0.091 |

As shown in Table 3, the joint preparations permit determination of the oxygen delivery, oxygen consumption and oxygen extraction rate of the joint cells. These values are not otherwise obtainable using intact animals because an accurate measurement of all blood flow in and out of the vascular system of the joint not possible in intact animal and because values, such as $PaO_2$, $PvO_2$ and hemoglobin content attribute only to joints, are not measurable in the intact animal.

Also as shown in Table 3, the isolated joints of the joint preparation examples 1 and 2 which had received interleukin 1 consumed more oxygen than the isolated joints of examples 3 and 4 which did not receive interleukin. The extraction of oxygen by cells and thus the metabolic activity was also greater in the isolated joints of examples 1 and 2 for 3 hours after injection of interleukin 1, even though the delivery of oxygen to the isolated joints in all of these joint preparations was the same. Thus, the joint preparation enables direct measurement of the partial pressure of oxygen in perfusate which flows into and out of the of the isolated joint permits specific is determination of the effect of chemical agents on the metabolic activity of the joint cells.

TABLE 4

FITC-DEXTRAN CONCENTRATION IN PERFUSATE EXITING THE ISOLATED JOINT AT VARIOUS TIMES (MIN) FOLLOWING INJECTION INTO THE SYNOVIAL CAVITY

| Time (min.) | Example 1 Innervated Inflamed Conc. (µg/ml) | Example 2 Denervated Inflamed Conc. (µg/ml) |
|---|---|---|
| BL | 1.510 | 1.124 |
| 2 | 1.507 | 1.348 |
| 4 | 1.468 | 1.268 |
| 6 | 1.513 | 1.266 |
| 8 | 1.489 | 1.443 |
| 10 | 1.507 | 1.209 |
| 12 | 1.385 | 1.257 |
| 14 | 1.414 | 1.308 |
| 16 | 1.382 | 1.228 |
| 18 | 1.351 | 1.353 |
| 20 | 1.452 | 1.388 |
| 25 | 1.436 | 1.351 |
| 30 | 1.341 | 1.353 |

TABLE 4-continued

FITC-DEXTRAN CONCENTRATION IN PERFUSATE EXITING THE ISOLATED JOINT AT VARIOUS TIMES (MIN) FOLLOWING INJECTION INTO THE SYNOVIAL CAVITY

| (Time) MIN. | Example 3 Innervated, Normal Conc. (μg/ml) | Example 4 Denervated, Normal Conc. (μg/ml) |
|---|---|---|
| BL | 1.102 | 0.810 |
| 2 | 1.124 | 0.853 |
| 4 | 1.021 | 0.810 |
| 6 | 1.036 | 0.865 |
| 8 | 1.094 | 0.812 |
| 10 | 1.048 | 0.778 |
| 12 | 1.058 | 0.759 |
| 14 | 1.057 | 0.698 |
| 16 | 0.889 | 0.809 |
| 18 | 0.842 | 0.901 |
| 20 | 0.927 | 0.83 |
| 25 | 0.949 | 0.823 |
| 30 | 0.880 | 0.868 |

Table 4 shows the average concentration of FITC-dextran in the perfusate flowing from the isolated joint in the joint preparations of examples 1A, 2A, 3A, and 4A following injection of the FITC-dextran into the synovial cavity of the isolated joints. As shown in Table 3, a greater concentration of dextran was released by inflamed joints that received interleukin 1. At 2 minutes after injection the concentration of dextran in the blood samples from the normal isolated joints of the joint preparations of examples 3 and 4 was only 0.95 μg/ml, when the concentration in dextran in the blood flowing from the inflamed denervated and innervated isolated joints in the joint preparations of examples 1 and 2 was 1.5 μg/ml and 1.3 μg/ml, respectively. The increased release of dextran from the inflamed joints is primarily due to increased permeability of the synovial membrane.

The joint preparation enables the direct measurement of release of chemical agent from the joint which is particularly useful in determining of the release of anti-inflammatory drugs from inflamed and non-inflamed joints in a patient either veterinary or human.

Determining the amount of drug released is of particular use in determining maximum dosages of toxic drugs to be injected into synovial cavities.

TABLE 5

| Time (Min) | Perfusate Flow (ml/min) | SEM | FITC Content μg | SEM |
|---|---|---|---|---|
| Example 1 Inflamed-Innervated | | | | |
| B1 | 3.16667 | 0.928679 | 6.1224 | 2.590353 |
| T2 | 3.16667 | 0.928679 | 5.855267 | 2.796246 |
| T4 | 3.16667 | 0.928679 | 5.569167 | 2.301927 |
| T6 | 3.16667 | 0.928679 | 5.726033 | 2.53563 |
| T8 | 3.16667 | 0.928679 | 5.5799 | 2.297229 |
| T10 | 3.16667 | 0.928679 | 5.8676 | 2.513471 |
| T12 | 3.16667 | 0.928679 | 5.3339 | 2.391611 |
| T14 | 3.16667 | 0.928679 | 5.358133 | 2.327032 |
| T16 | 3.16667 | 0.928679 | 4.982033 | 1.863925 |
| T18 | 3.16667 | 0.928679 | 4.874067 | 2.006873 |
| T20 | 3.16667 | 0.928679 | 5.257633 | 1.947954 |
| T25 | 3.16667 | 0.928679 | 5.1438 | 1.920142 |
| T30 | 3.16667 | 0.928679 | 4.9281 | 2.029067 |

TABLE 5-continued

| Time (Min) | Perfusate Flow (ml/min) | SEM | FITC Content μg | SEM |
|---|---|---|---|---|
| Example 2 Inflamed-Denervated | | | | |
| B1 | 2.726667 | 0.859871 | 3.2134 | 1.160747 |
| T2 | 2.726667 | 0.859871 | 4.019933 | 1.565697 |
| T4 | 2.726667 | 0.859871 | 3.667817 | 1.378385 |
| T6 | 2.726667 | 0.859871 | 3.74615 | 1.413846 |
| T8 | 2.726667 | 0.859871 | 4.482417 | 1.662618 |
| T10 | 2.726667 | 0.859871 | 3.42165 | 1.234801 |
| T12 | 2.726667 | 0.859871 | 3.85223 | 1.599963 |
| T14 | 2.726667 | 0.859871 | 3.916007 | 1.550408 |
| T16 | 2.726667 | 0.859871 | 3.922613 | 1.595886 |
| T18 | 2.726667 | 0.859871 | 4.120823 | 1.570835 |
| T20 | 2.726667 | 0.859871 | 4.023147 | 1.546662 |
| T25 | 2.726667 | 0.859871 | 4.022463 | 1.574821 |
| T30 | 2.726667 | 0.859871 | 3.834807 | 1.489941 |
| Example 3 Control Inervated | | | | |
| B1 | 2.476667 | 0.97551 | 2.96075 | 1.373655 |
| T2 | 2.476667 | 0.97551 | 2.955547 | 1.331134 |
| T4 | 2.476667 | 0.97551 | 2.497963 | 1.102618 |
| T6 | 2.476667 | 0.97551 | 2.4776 | 1.075971 |
| T8 | 2.476667 | 0.97551 | 2.86786 | 1.325052 |
| T10 | 2.476667 | 0.97551 | 2.499283 | 1.065194 |
| T12 | 2.476667 | 0.97551 | 2.750847 | 1.299588 |
| T14 | 2.476667 | 0.97551 | 2.944487 | 1.351815 |
| T16 | 2.476667 | 0.97551 | 2.31335 | 1.160793 |
| T18 | 2.476667 | 0.97551 | 1.792819 | 0.739579 |
| T20 | 2.476667 | 0.97551 | 2.319029 | 1.148 |
| T25 | 2.476667 | 0.97551 | 2.491397 | 1.15237 |
| T30 | 2.476667 | 0.97551 | 2.32934 | 1.159631 |
| Example 4 Control Denervated | | | | |
| B1 | 1.815 | 0.561829 | 1.384315 | 0.4343798 |
| T2 | 1.815 | 0.561829 | 1.518725 | 0.5050618 |
| T4 | 1.815 | 0.561829 | 1.365403 | 0.4302443 |
| T6 | 1.815 | 0.561829 | 1.38785 | 0.3607932 |
| T8 | 1.815 | 0.561829 | 1.358085 | 0.4305707 |
| T10 | 1.815 | 0.561829 | 1.156033 | 0.2991582 |
| T12 | 1.815 | 0.561829 | 1.205568 | 0.3332989 |
| T14 | 1.815 | 0.561829 | 1.11601 | 0.3299595 |
| T16 | 1.815 | 0.561829 | 1.344187 | 0.3916747 |
| T18 | 1.815 | 0.561829 | 1.4882 | 0.4139172 |
| T20 | 1.815 | 0.561829 | 1.410817 | 0.4134367 |
| T25 | 1.815 | 0.561829 | 1.424233 | 0.4915524 |
| T30 | 1.815 | 0.561829 | 1.365037 | 0.3883909 |

Table 5 shows the average perfusate flowing from in the isolated joints of examples 1A, 2A, 3A, and 4A following injection of FITC-dextran and the average amount of dextran released into the vascular system of the joint of the preparations. As shown in table 5, the release of small quantities of FITC-dextran from the synovial cavity into the vascular system of the isolated joint are detectable within two minutes after administration of the dextram to isolated, joints of examples 3A and 4 that did not receive interleukin 1. The amount of dextran released by the joints of examples 3A and 4A was 2.9 and 1.3 μg, respectively. The release of dextran into the vascular system from inflamed isolated joints of examples 1 and 2 that received interleukin 1 was 5.8 and 4.0 μg, respectively. Thus, the joint preparations are useful for detecting and measuring the release of even small amounts chemical agents from the synovial cavity of the isolated joint. Average perfusate flow values permit determination of rate of release. Accordingly, the joint preparation permits the measurement the release of chemical agents from the synovial cavity of the isolated joint is useful for determining the loss of chemical agents from healthy and inflamed joint of a patient into the systemic circulation of the patient. By determining rate of loss, the interval between injections of inflammatory drugs can be determined so as to maintain a desired concentration of drug in the synovial cavity.

The histological examination of the tissues from isolated joints of examples 1B and 2B which received interleukin 1, exhibited greater albumin fluorescence than the isolated joints of examples 3B and 4B which did not receive interleukin 1. These histological examinations also showed that the distribution of albumin fluorescence was higher in villous than in fibrous synovial membrane of the inflamed joints, establishing that the joint preparations are also useful for identifying the pathways that indicators of synovial membrane permeability travel in inflamed joints as compared to non-inflamed joints.

While the invention has been described to some degree of particularity, various adaptations and modifications can be made without departing from the scope of the invention as defined in the appended claims.

What is claimed is:

1. A joint preparation free of the host animal, comprising:
   (a) an isolated joint;
   (b) a perfusate for perfusing said isolated joint;
   (c) an oxygenator in fluid communication with the perfusate for oxygenating the perfusate;
   (d) an inflow conduit having a first end and a second end, the first end in communication with said isolated joint for introducing said perfusate into said isolated joint;
   (e) an outflow conduit having a first end and a second end, the first end in fluid communication with the isolated joint for receiving perfusate from the joint, the second end in fluid communication with the second end of the inflow conduit; and
   (f) a pump in communication with the inflow conduit or outflow conduit for pumping the perfusate through said isolated joint.

2. The joint preparation of claim 1 further comprising a reservoir for holding the perfusate, said reservoir in fluid communication with the inflow conduit and the outflow conduit.

3. The joint preparation of claim 1 wherein said outflow conduit comprises tubing connected to the veins of the joint vascular system.

4. The isolated joint preparation of claim 1 further comprising a weight measuring system operatively connected with said isolated joint for weighing said isolated joint.

5. A method for measuring the release of a chemical agent from the synovial cavity of a joint to the vascular system of the joint, comprising the following steps:
   (a) providing the joint preparation of claim 1,
   (b) injecting the chemical agent into the synovial cavity of the isolated joint;
   (c) withdrawing an aliquot of perfusate from the outflow conduit;
   (d) measuring the concentration of said chemical agent in the aliquot.

6. The method of claim 5, wherein said joint preparation further comprises a perfusate flow measuring device in fluid communication with to said outflow conduit;
   and further comprising the steps of:
   measuring the rate of flow of perfusate from the veins of said isolated joint; and
   calculating the rate of release by dividing the concentration of the chemical agent in the perfusate by the rate of flow of perfusate.

7. The method of claim 5 wherein the joint preparation comprises an isolated equine metacarpophalangeal joint.

8. A method for measuring the partial arterial oxygen pressure and partial venous oxygen pressure of a single joint, comprising:
   (a) providing the joint preparation of claim 1;
   (b) withdrawing an aliquot of perfusate from the inflow conduit;
   (c) measuring the partial pressure of oxygen in the first aliquot of perfusate to determine the partial arterial oxygen pressure of said isolated joint;
   (d) withdrawing an aliquot of perfusate from said outflow conduit;
   (e) measuring the partial pressure of oxygen in the second aliquot to determine the partial venous oxygen pressure of said isolated joint.

9. The method of claim 8 further comprising the steps of:
   (i) measuring the rate of flow of said perfusate into said isolated joint;
   (ii) measuring the temperature of said isolated joint;
   (iii) measuring the weight of said isolated joint
   (iv) measuring the hemoglobin content of said perfusate;
   (v) measuring the hemoglobin saturation concentration of said perfusate;
   (vi) calculating the amount of oxygen delivered to the joint.

10. A method for measuring the effect of a drug on the permeability of the synovial membrane of a joint, comprising:
    (a) providing the isolated joint preparation of claim 1;
    (b) injecting a drug into the synovial cavity of the isolated joint:
    (c) injecting an indicator compound having a molecular weight of at least 40,000 daltons into the synovial cavity of the isolated joint;
    (d) withdrawing an aliquot of perfusate from the outflow conduit; and
    (e) assaying for the presence of the indicator compound.

11. The method of claim 10 wherein the joint preparation comprises an isolated equine metacarpophalangeal joint.

12. The isolated joint preparation of claim 1 wherein the isolated joint is an isolated equine metacarpophalangeal joint.

13. A joint preparation in fluid communication with a host animal comprising:
    (a) an isolated joint;
    (b) a perfusate for perfusing said isolated joint;
    (c) an inflow conduit having a first end and a second end, the first end in fluid communication with the isolated joint and a second end in fluid communication with the host animal;
    (d) an outflow conduit for receiving the perfusate from said isolated joint, said outflow conduit having a first end in fluid communication with said isolated joint and a second end, said second ends of each of said inflow and outflow conduits being connected to the host animal to provide fluid flow from said first conduit through said joint and to said second conduit.

14. The joint preparation of claim 13 further comprising a first pump connected to the inflow conduit for pumping said perfusate into said isolated joint.

15. The joint preparation of claim 13 further comprising a second pump in fluid communication with the outflow conduit for pumping said perfusate from said outflow conduit into the host animal.

16. A method for evaluating the effect of a chemical agent on an isolated joint comprising:

(a) providing the joint preparation of claim 2 (b) measuring at least two of the following physiological parameters of arterial pressure, venous pressure, capillary pressure, $PaO_2$, $VaO_2$, weight of the joint, amount of synovial fluid produced by said isolated joint, concentration of white blood cells in the synovial fluid, concentration of protein in the perfusate fluid, concentration of protein in the synovial fluid, concentration of albumin in the perfusate fluid, concentration of albumin in the synovial fluid, rate of flow of perfusate into the arteries of said joint, rate of flow of said perfusate from the veins of said joint, perfusate flow to the synovium, synovial membrane permeability;

(c) injecting the chemical agent into the synovial cavity of the isolated joint; and (d) measuring the physiological parameters of step (b) to determine the effect of the chemical agent on said selected physiological parameters.

17. The method of claim 16 wherein at least two of said physiological parameters are measured simultaneously.

18. The method of claim 16 wherein said joint preparation further comprises a fluid flow measuring device connected to said outflow conduit and wherein at least one of said physiological parameters is the rate of flow of perfusate from said isolated joint.

19. The method of claim 16 wherein the joint preparation comprises an isolated equine metacarpophalangeal joint.

20. The joint preparation of claim 13 wherein the isolated joint is an isolated equine metacarpophalangeal joint and the host animal is a horse.

* * * * *